US011827660B2

(12) United States Patent
Seifert

(10) Patent No.: US 11,827,660 B2
(45) Date of Patent: Nov. 28, 2023

(54) SYNTHESIS STRATEGY FOR GAP PROTECTING GROUP

(71) Applicant: Sederma, Le Perray-en-Yvelines (FR)

(72) Inventor: Cole Seifert, Le Perray-en-Yvelines (FR)

(73) Assignee: Sederma, Le Perray-en-Yvelines (FR)

(*) Notice: Subject to any disclaimer, the term of this patent is extended or adjusted under 35 U.S.C. 154(b) by 0 days.

(21) Appl. No.: 17/310,186

(22) PCT Filed: Jan. 26, 2020

(86) PCT No.: PCT/US2020/015132
§ 371 (c)(1),
(2) Date: Jul. 23, 2021

(87) PCT Pub. No.: WO2020/159837
PCT Pub. Date: Aug. 6, 2020

(65) Prior Publication Data
US 2022/0089619 A1    Mar. 24, 2022

Related U.S. Application Data

(60) Provisional application No. 62/800,142, filed on Feb. 1, 2019.

(51) Int. Cl.
| C07F 9/30 | (2006.01) |
| C07F 9/32 | (2006.01) |
| C07F 9/36 | (2006.01) |
| C07F 9/53 | (2006.01) |
| C07K 1/02 | (2006.01) |
| C07K 1/06 | (2006.01) |
| C07F 9/28 | (2006.01) |

(52) U.S. Cl.
CPC ............ *C07F 9/28* (2013.01); *C07F 9/304* (2013.01); *C07F 9/3229* (2013.01); *C07F 9/36* (2013.01); *C07F 9/5325* (2013.01); *C07K 1/02* (2013.01); *C07K 1/062* (2013.01)

(58) Field of Classification Search
CPC ......... C07F 9/28; C07F 9/304; C07F 9/3229; C07F 9/36; C07F 9/5325; C07K 1/02; C07K 1/062
See application file for complete search history.

(56) References Cited

U.S. PATENT DOCUMENTS

| 4,617,584 A | 10/1986 | Ikeya et al. |
| 5,516,891 A | 5/1996 | Siwruk et al. |
| 6,753,409 B1 | 6/2004 | Chrzan et al. |
| 8,093,435 B2 | 1/2012 | Chiba et al. |
| 8,383,770 B2 | 2/2013 | Dalton et al. |
| 8,633,298 B2 | 1/2014 | Chiba et al. |
| 8,716,439 B2 | 5/2014 | Murao et al. |
| 9,353,148 B2 | 5/2016 | Takahashi |
| 10,947,267 B2 * | 3/2021 | Li .................... C07K 1/062 |
| 2001/0018512 A1 | 8/2001 | Blanchard |
| 2003/0018164 A1 | 1/2003 | Eggen et al. |
| 2004/0214989 A1 | 10/2004 | Chiba et al. |
| 2008/0287649 A1 | 11/2008 | Chen et al. |
| 2009/0069538 A1 | 3/2009 | Murao et al. |
| 2009/0299103 A1 | 12/2009 | Chiba et al. |
| 2010/0029904 A1 | 2/2010 | Chiba et al. |
| 2010/0240867 A1 | 9/2010 | Takahashi |
| 2010/0249374 A1 | 9/2010 | Takahashi |
| 2014/0100355 A1 | 4/2014 | Acemoglu et al. |
| 2014/0178302 A1 | 6/2014 | Lattuada et al. |
| 2014/0213814 A1 | 7/2014 | Monnaie et al. |
| 2015/0023987 A1 | 1/2015 | Borch et al. |
| 2016/0053179 A1 | 2/2016 | Takata et al. |
| 2016/0165916 A1 * | 6/2016 | Howell .................. A23L 27/88 426/594 |
| 2016/0257725 A1 | 9/2016 | Verdine et al. |
| 2018/0215782 A1 | 8/2018 | Kono et al. |
| 2019/0330262 A1 | 10/2019 | Li et al. |

FOREIGN PATENT DOCUMENTS

| EP | 2716650 A1 | 4/2014 |
| EP | 3778621 A1 | 2/2021 |
| JP | 2003500415 A | 1/2003 |
| JP | 2003055396 A | 2/2003 |
| JP | 2003183298 A | 7/2003 |
| JP | 2003183298 A | 7/2003 |
| JP | 2004059509 A | 2/2004 |
| WO | 9325571 A1 | 12/1993 |
| WO | 0071569 A1 | 11/2000 |
| WO | 2007034812 A1 | 3/2007 |

(Continued)

OTHER PUBLICATIONS

Crich et al. Dichotomous Reaction Pathways In The Reaction Of Triarylphosphine Oxides With Meerwein's Salt. Tetrahedron Letters. 1989, vol. 30, No. 4, pp. 475-476. (Year: 1989).*

Zhang et al. Ni(II)/Zn Catalyzed Reductive Coupling of Aryl Halides with Diphenylphosphine Oxide in Water. Organic Letters. 2011, vol. 13, No. 13, pp. 3478-3481. (Year: 2011).*

Granoth et al. A Monocyclic Phosphorane Oxide Anion and the Extraordinary Reactivity of its Tautomeric Phosphine Oxide Alkoxide. Journal of the Chemical Society, Chemical Communications. 1981, pp. 981-982 (Year: 1981).*

Sukhorukov et al. Rearrangement of phosphinotriphenylcarbinol. Izvestiya Akademii Nauk SSSR, Seriya Khimicheskaya (1975), (2), pp. 463-465—Abstracted in HCAPLUS 1975:410287. (Year: 1975).*

(Continued)

*Primary Examiner* — Jeffrey E. Russel
(74) *Attorney, Agent, or Firm* — RatnerPrestia

(57) ABSTRACT

The present invention relates to a novel synthesis method to form particular molecules. These molecules have multiple uses, most notably in the field of protecting groups used throughout organic and synthetic chemistry. The disclosed method is safer, more cost- and time-effective, and more amenable to large scale production than those currently known in the art. The protecting groups synthesized are useful in GAP peptide synthesis.

12 Claims, 4 Drawing Sheets

(56) References Cited

FOREIGN PATENT DOCUMENTS

| | | | |
|---|---|---|---|
| WO | 2007099656 A1 | 9/2007 |
| WO | 2007122847 A1 | 11/2007 |
| WO | 2010104169 A1 | 9/2010 |
| WO | 2010113939 A1 | 10/2010 |
| WO | 2011152603 A1 | 12/2011 |
| WO | 2013117440 A1 | 8/2013 |
| WO | 2014093723 A2 | 6/2014 |
| WO | 2017112809 | 8/2018 |
| WO | 2019198834 A1 | 10/2019 |
| WO | 2019217116 A1 | 11/2019 |
| WO | 2019231760 A1 | 12/2019 |
| WO | 2022115825 A1 | 6/2022 |
| WO | 2020159837 A1 | 8/2022 |
| WO | 2022226536 A1 | 10/2022 |

OTHER PUBLICATIONS

Suresh Pindi, Parminder Kaur, Gaurav Shakya and Guigen Li; N-Phosphinyl Imine Chemistry (I): Design andSynthesis of Novel N-Phosphinyl Imines and their Application to Asymmetric aza-Henry Reaction; Chem Biol Drug Des 2011; 77: 20-29; Sep. 19, 2010; Chemical Biology & Drug Design.
Takayuki Shioiri; Recent Advances of Protective Groups in Peptide Synthesis; Journal of Synthetic Organic Chemistry, 1978, 36(9), 740-748.
Teng Ai, Guigen Li; Chiral N-phosphonyl imine chemistry: Asymmetric synthesis of a,b-diamino esters by reacting phosphonyl imines with glycine enolates; Bioorganic & Medicinal Chemistry Letters 19 (2009) 3967-3969;Mar. 5, 2009; Published by Elsevier Ltd.
Tingting Fu, Hongwei Qiao, Zhimin Peng, Gaobo Hu, Xueji Wu, Yuxing Gao and Yufen Zhao; Palladium-catalyzed air-based oxidative coupling of arylboronic acids with H-phosphine oxides leading to aryl phosphine oxides; Org. Biomol. Chem.; Feb. 26, 2014 ; The Royal Society of Chemistry12, 2895-2902.
Wuts, P. G. M. Greene's Protective Groups in Organic Synthesis. 5 ed.; John Wiley & Sons, Inc: New Jersey, 2014.
Adiseshu Kattuboina, Parminder Kaur, Thao Nguyen, Guigen Li; Chiral N-phosphonyl imine chemistry: asymmetric 1,2-additionsof allylmagnesium bromides; Tetrahedron Letters 49 (2008) 3722-3724; Elsevier Ltd.
Adriano Mollicaa, Francesco Pinnen, Stefanucci Azzurra and Roberto Costante; The Evolution of Peptide Synthesis: From Early Days to Small Molecular Machines; Current Bioactive Compounds 2013, pp. 184-202, vol. 9, No. 3; Bentham Science Publishers.
Bachem. Tips and Trick for Solid Phase Peptide Synthesis from the Experts at Bachem. Solid Phase Peptide Synthesis 2016, pp. 1-55.
Chun-Chi Chen, Basker Rajagopal, Xuan Yu Liu, Kuan Lin Chen, Yu-Chang Tyan, Ful Lin, Po-Chiao Lin; A mild removal of Fmoc group using sodium azide; Amino Acids (2014) 46:367-374; Springer-Verlag Wien.
Clara Brieke and Max J. Cryle; A Facile Fmoc Solid Phase Synthesis Strategy To Access Epimerization-Prone Biosynthetic Intermediates of Glycopeptide Antibiotics; Org. Lett. 2014, 16, 2454-2457; American Chemical Society.
Daisuke Takahashi et al.; Development of an efficient liquid-phase peptide synthesis protocol using a novel fluorene-derived anchor support compound with Fmoc chemistry; AJIPHASE; Tetrahedron Letters; 53 (2012) 1936- 1939.
Daisuke Takahashi et al; Novel diphenylmethyl-Derived Amide Protecting Group for Efficient Liquid-Phase Peptide Synthesis: AJIPHASE; Organic Letters; 2012; vol. 14, No. 17; 4514-4517.
Daisuke Takahashi; Ajiphaseu: A Highly Efficient Synthetic Method for One-Pot Peptide Elongation in the Solution Phase by an Fmoc Strategy; Angew. Chem. Int. Ed. 2017; 56; 7803-7807.
David Dailler, Gregory Danoun and Olivier Baudoin; A General and Scalable Synthesis of Aeruginosan Marine Natural Products Based on Two Strategic C(sp3)-H Activation Reactions; Angew. Chem. Int. Ed. 2015, 54, 1-5; Wiley-VCH Verlag GmbH & Co. KGaA, Weinheim.
De Marco et al. "C > N and N >C Solution Phase Peptide Synthesis Using the N-acyl 4-Nitrobenzenesulfonamide as Protection of the Carboxylic Function"; Organic and Biomolecular Chemistry, Jul. 21, 2013, vol. 11, Iss. 23, pp. 3786-3796.
Elias Kaufmann, Hiromu Hattori, Hideki Miyatake-Ondozabal and Karl Gademann; Total Synthesis of the Glycosylated Macrolide Antibiotic Fidaxomicin; Organic Letters; Jun. 1, 2015; 17; 3514-3517; ACS AuthorChoice.
European Search Report (EP 16880050.6) dated May 27, 2019.
Guanghui An, Cole Seifert and Guigen Li; N-Phosphonyl/phosphinyl imines and groupassistedpurification (GAP) chemistry/technolog; Organic & Biomolecular Chemistry; Dec. 9, 2014;p. 1-18; The Royal Society of Chemistry www.rsc.org/obc.
Guanghui An, Cole Seifert, Hao Sun, Yi Pan, and Guigen Li; Group-Assisted Purification (GAP) for Protection of Amino Acids Using N-Phosphonyl Functional Groups; Heterocycles, vol. 90, No. 1, 2015; pp. 344-356; The Japan Institute of Heterocyclic Chemistry.
Guanghui An, Wei Zhou, Xiaokang Xu, Yi Pan and Guigen Li; Solution-Phase-Peptide Synthesis Without Purification Of Column Chromatography And Recrystallization By Protecting Amino Acid Esters With Phosphinyl Chloride; HETEROCYCLES, vol. 90, No. 2, 2015, pp. 1405-1418; The Japan Institute of Heterocyclic Chemistry.
Haruaki Yajima; Synthetic Aspects of Peptides; Journal of Synthetic Organic Chemistry, 1974, 32(10), 826-832.
Hou et al. "Progress in Chemical Synthesis of Peptides and Proteins"; Transactions of Tiajin University; Jun. 23, 2017, vol. 23, Iss.5, pp. 401-419.
Information Disclosure Statement; U.S. Appl. No. 15/555,484, filed Jul. 7, 2020 ; 3 pgs.
Information Disclosure Statement; U.S. Appl. No. 15/555,484, filed Sep. 1, 2017; 5 pgs.
International Search Report; PCT/JP2016/056319 dated May 31, 2016; 2 pgs; Japan Patent Office.
International Search Report; PCT/US2016/068112; dated May 8, 2017; pp. 1-3.
International Search Report; PCT/US2019/029569; dated Jul. 12, 2009; pp. 1-2.
International Search Report; PCT/US2019/033296; dated Jul. 15, 2009; p. 1.
International Search Report; PCT/US2020/15132; dated Jun. 4, 2020 pp. 1-3.
Isidro-Llobet, Albert, Mercedes Alvarez and Fernando Albericio; Amino Acid-Protecting Groups; Chem. Rev. 2009, 109, 2455-2504; American Chemical Society.
Ivo F. Eggen et al.; A novel method for repetitive peptide synthesis in solution without isolation of intermediates; J. Peptide Sci. 11; (2005); 633-641 .
James E. Sheppeck; A convenient and scaleable procedure for removing the Fmocgroup in solution; Tetrahedron Letters 41 (2000) 5329-53333.
Janssen, M.C.C.; Vogt, D.; Müller, C.; 'Click' dendritic phosphines: design, synthesis, application in Suzuki coupling, and recycling by nanofiltration; Catalysis and Organometallic Chemistry; Department of Chemical Engineering and Chemistry; Advanced Synthesis & Catalysis, 351(3), 313-318. Wiley-VCH Verlag. ISSN 1615-4150; (2009).
Jensen, Knud J. Chapter 1: Peptide Synthesis. Pharmaceutical Formulation Development of Peptides and Proteins 2013, pp. 1-16.; CRC Press/Taylor & Francis Group, 2013; Boca Raton, FL.
Jianbin Wu, Guanghui An, Siqi Lin, Jianbo Xie, Wei Zhou, Hao Sun, Yi Pana and Guigen Li; Solution-phase-peptide synthesis via the group-assisted purification (GAP) chemistry without using chromatography and recrystallization;Chem. Commun., 2014, 50, 1259-1261; The Royal Society of Chemistry.
Jian-Bo Xie, Jian Luo, Timothy R. Winn, David B. Cordes and Guigen Li; Group-assisted purification (GAP) chemistry for thesynthesis of Velcade via asymmetric borylation of N-phosphinylimines; Beilstein

(56) References Cited

OTHER PUBLICATIONS

Journal Organic Chemistry; Mar. 31, 2014; Beilstein J. Org. Chem. 2014, 10, 746-751; Beilstein-Institut.

Jianlin Han, Teng Ai, Thao Nguyen and Guigen Li;Chiral N-Phosphonyl Imine Chemistry: Asymmetric Additions of Ester Enolates for the Synthesis of b-Amino Acids; Chem Biol Drug Des 2008; 72: 120-126; Blackwell Publishing Limited.

Kattuboina, A. et al. "Chiral N-phosphonyl imine chemistry: new reagents and their applications for asymmetric reactions." Tetrahedron Lett. 2008, 49, 1573-1577.

Louis A. Carpino et al; Rapid, Continuous Solution-Phase Peptide Synthesis: Application to Peptides of Pharmaceutical Interest; Organic Process Research & Development 2003, 7, 28-37.

Mariagiovanna Spinella, Rosaria De Marco, Emilia L. Belsito, Antonella Leggio, Angelo Liguori; The dimethylsulfoxonium methylide as unique reagent for the simultaneous deprotection of amino and carboxyl function of N-Fmoc-rx-amino acid and N-Fmoc-peptide esters; Tetrahedron 69 (2013) 2010-2016; Elsevier Ltd.

Masayoshi Mochizuki, Shugo Tsuda, Kyoko Tanimura, and Yuji Nishiuchi; Regioselective Formation of Multiple Disulfide Bonds with the Aid of Postsynthetic S-Tritylation; Organic Letters; Apr. 10, 2015; 17; pp. 2202-2205; American Chemical Society.

Meiyun Shi, Yan Yang, Xiaotong Zhou, Lanlan Cai, Chunxue Fang, Can Wang, Heping Sun, Yantong Sun, Yin Gao, Jingkai Gu, J. Paul Fawcett; Determination of thymopentin in beagle dog blood by liquid chromatography with tandem mass spectrometry and its application to a preclinical pharmacokinetic study; J. Sep. Sci. 2015, 38, pp. 1351-1357; WILEY-VCH Verlag GmbH & Co. KGaA, Weinheim.

Ming-Xia Zhu, Wen-Li Wan, Hai-Shen Li, Jing Wang, Gui-An Chen, Xiao-Yan Ke; Thymopentin enhances the generation of T-cell lineage derived from human embryonic stem cells in vitro; Experimental Cell Research 331 ( 2015) 387-398; Elsevier Inc.

Muriel Amblard, Jean-Alain Fehrentz, Jean Martinez and Gilles Subra; Methods and Protocols of Modern Solid Phase Peptide Synthesis; Molecular Biotechnology; pp. 239-254; vol. 33, 2006; Humana Press Inc.

Padmanabha v. Kattamuri, Teng Ai, Suresh Pindi, Yinwei Sun, Peng Gu, Min Shi, and Guigen Li; Asymmetric Synthesis of a.-Amino-1,3-dithianes via Chiral N-Phosphonyl Imine-Based Umpolung Reaction Without Using Chromatography and Recrystallization; The Journal of Organic Chemistry; Mar. 15, 2011; pp. 2792-2797; vol. 76; pubs.acs.org/joc.

Parminder Kaur, Walter Wever, Suresh Pindi, Raizada Milles, Peng Gu, Min Shi and Guigen Li; The GAL Chemistry for Chiral N-phosphonyl imine-based Strecker reaction; Green Chem., 2011, 13, 1288; The Royal Society of Chemistry.

Pradeep K Sharma, Leo J. Romanczyk, Jr., Leelakrishna Kondaveti, Bollu Reddy, Jeeva Arumugasamy, Richard Lombardy, Yanni Gou, and Hagen Schroeter; Total Synthesis of Proanthocyanidin A 1, A2, and Their Stereoisomers; Organic Letters; Mar. 4, 2015; 17, 2306-2309; American Chemical Society.

Pubchem. CID 129303937; Aug. 4, 2017; pp. 1-11. Retrieved from the Internet ; p. 2.

Pubmed Compound Summary for CID 71676245, 'AKOS016034578', U.S. National Library of Medicine, Sep. 4, 2013 (Sep. 4, 2013), p. 3.

R. B. Merrifield; Solid Phase Peptide Synthesis I. The Synthesis of a Tetrapeptide;. J. Am. Chem. Soc. 1963; pp. 2149-2154; vol. 85.

Raymond Behrendt, Simon Huber, Roger Marti and Peter White; New t-butyl based aspartate protecting groups preventing aspartimide formation in Fmoc SPPS; Journal of Peptide Science; Jun. 15, 2015; 21: 680-687; European Peptide Society and John Wiley & Sons, Ltd.

Saranya Chandrudu, Pavla Simerska and Istvan Toth; Chemical Methods for Peptide and Protein Production; Molecules Open Access Article; Apr. 12, 2013; pp. 4373-4388; Creative Commons Attribution.

Seifert et al. "GAP Peptide Synthesis via Design of New Gap Protecting Group: An Fmoc/tBu Synthesis of Thymopentin Free from Polymers, Chromatograpy and Recrystallization", European Journal of Organic Chemistry, Mar. 8, 2016; vol. 2016, Iss. 9, pp. 1714-1719.

Shelton, P. T.; Jensen, K; Linkers, Resins, and General Procedures for Solid-Phase Peptide Synthesis. In Peptide Synthesis and Applications, 2nd Edition, Jensen, K. J.; Shelton, P. T.; Pedersen, S. L., Eds. Humana Press Inc: Totowa, 2013; vol. 1047, pp. 23-41.

Stefan B. Lawrenson, Roy Arav and Michael North; The greening of peptide synthesis; Green Chem., 2017, 19, 1685-1691; The Royal Society of Chemistry.

International Search Report and Written Opinion for International Application No. PCT/US2021/072297, dated Mar. 17, 2022, 11 pages.

International Search Report and Written Opinion for International Application No. PCT/US2022/071870, dated Sep. 1, 2022, 11 pages.

Wu et al., "Solution-Phase-Peptide Synthesis Via the Group Assisted Purification (GAP) Chemistry Without Using Chromatography and Recrystallization", Chemical Communications, Feb. 7, 2014, vol. 50, No. 10, pp. 1-9.

PUBCHEM, Substance Record for SID 135946876, Modify Date Jan. 25, 2017, retrieved from the Internet at http://pubchem.ncbi.nlm,nih.gov/substance/135946876, 6 pages.

Seifert et al., "Asymmetric Carbamoyl Anion Additions to Chiral N-Phosphonyl Imines Via the GAP Chemistry Process and Stereoseiectivity Enrichments", The Journal of Organic Chemistry, 2015, vol. 80, pp. 447-452.

Seki et al., "Cellular Protection of SNAP-25 Against Botuiinum Neurotoxin/A: Inhibition of Thioredoxin Reductase Through a Suicide Substrate Mechanism", Journal of the American Chemical Society, 2016, vol. 138, No. 17, pp. 5368-5575.

Seki et al. Supporting information for "Cellular Protection of SNAP-25 Against Botuiinum Neurotoxin/A: Inhibition of Thioredoxin Reductase Through a Suicide Substrate Mechanism", 2016, pp. 1-43.

\* cited by examiner

Pg = Cbz, Fmoc, Boc, etc.
W = general variable
R = remaining protecting group structure from FIG. 5
coupling reagent = TFFH, EDC, etc.

SYNTHESIS STRATEGY FOR GAP PROTECTING GROUP

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

CROSS-REFERENCE TO RELATED APPLICATIONS

This application cross-references: i) WO Application No. WO2017112809A1 and WO Publication No. WO2017112809A1, "System and method for solution phase GAP peptide synthesis," filed on 21 Dec. 2016; ii) WO Application No. PCT/US19/29569, "Method for Solution-Phase Peptide Synthesis," filed Apr. 29, 2019; iii) U.S. Provisional Application No. 62/678,564, "Improved Protection Strategy for GAP Peptide Synthesis;" iv) WO Application No. PCT/US19/33296, "Method for Solution-Phase Peptide Synthesis and Protecting Strategies Thereof," filed on May 21, 2019; and v) U.S. Provisional Application No. 62/667,591, "Method for Solution-Phase Peptide Synthesis;" and these applications and publications are herein incorporated by reference as examples.

STATEMENT OF FEDERALLY SPONSORED RESEARCH OR DEVELOPMENT

None.

REFERENCE TO A SEQUENCE LISTING, A TABLE, OR A COMPUTER LISTING COMPACT DISC APPENDIX

None.

BACKGROUND OF THE INVENTION

Recent research efforts have made significant advancements in the area of purification chemistry, focusing specifically on avoiding column chromatography and recrystallization. This research has been defined as Group-Assisted Purification (GAP) chemistry/technology as a chemistry for organic synthesis that avoids traditional purification methods such as chromatography and/or recrystallization by purposefully introducing a well-functionalized group in the starting material or in the newly generated product. These GAP groups can also often be used as protecting groups to prevent undesired side-reactions during the synthesis of target molecules. Such research has the potential to encompass the entire field of synthetic organic chemistry.

Protecting groups are found in almost every complex synthesis where multiple functional groups are present. Effective protecting groups need to be robust to a wide variety of conditions and must be added and removed with high yield. In regards to GAP chemistry, an ideal example would be one in which a semi-permanent protecting group introduced the necessary solubility characteristics required for GAP. However, most traditional protecting groups are nonpolar, and therefore do not generate the required GAP solubility for most substrates. If a protecting group could be developed that generated adequate solubility control, then GAP chemistry could potentially be extended to all syntheses which require the use of that protecting group. Several approaches have been utilized. Published patent application WO 2014093723 A2, teaches the protection of imines with a GAP-equipped chiral auxiliary, then using these chiral, N-phosphonyl imines as electrophiles in asymmetric boron addition reactions. Purification was conducted via GAP processes. This work is valuable in that it provides facile access to chiral, $\alpha$-boronic acid amines, which could potentially be used to synthesize novel amino acid derivatives, which could potentially be incorporated into novel peptide targets.

Protecting groups are used extensively is in peptide synthesis, both for solid and solution phase approaches. For traditional peptide synthesis protection strategies, one of the most commonly used strategies is Fmoc/tBu. U.S. Pat. No. 8,383,770 B2 teaches the use of the Fluorenylmethoxycarbonyl (Fmoc) and tert-Butyloxycarbonyl (Boc) N-terminus protecting groups in Solid-Phase Peptide Synthesis (SPPS). This technology is well known and widely applied in industry. Boc and Fmoc groups have been used for decades in all areas of peptide chemistry, and the preferred Fmoc group is almost entirely restricted to solid phase. Developed by Merrifield in the 1960's, Solid-Phase Peptide Synthesis (SPPS) has become a standard protocol used by multiple scientific disciplines for research and manufacturing. The advantages of the polymer support lie in its ability to allow facile purification of the growing peptide after each coupling/deprotection step, which avoids the use of column chromatography. The key disadvantage of SPPS lies in the difficulty of scale-up: many polymer supports are expensive and occupy the vast majority of the mass of the material to be worked with; also, large excess of expensive solvents are required to swell the polymer resin, which takes up valuable reactor space.

Examples of economically feasible Fmoc protection schemes in solution are non-existent, with few examples in the literature at all. U.S. Pat. No. 5,516,891 A provides one of the few examples of Fmoc-based SolPPS. Again, the Fmoc peptide synthesis is almost entirely restricted to SPPS, due to the formation of N-fluorenylmethylpiperidine (NFMP) as a side product during deprotection, which is difficult to remove without polymer supports. The standard protocol for Fmoc deprotection is to stir the Fmoc-peptide in a solution of dimethylformamide (DMF) or dichloromethane (DCM) with excess piperidine, deprotecting the Fmoc group and forming NFMP in the process. The '891 patent teaches removal of this impurity by deprotecting with 4-aminomethylpiperidine (4AMP) instead of piperidine. This forms NFMP-$CH_2NH_2$ instead of NFMP, which due to the presence of the extra amino group, can be extracted into water. The problem with this method lies in the high cost of using 4AMP. This is why this method is cost prohibitive, and why it has not been accepted by the industry.

Another example of Fmoc-based SolPPS can be seen in published patent application WO2017112809A1. This patent teaches the use of a C-terminus group-assisted purification (GAP) protecting group, benzyl diphenylphosphine oxide (HOBnDpp), to control the solubility of the target peptide to allow for selective precipitation after each successive coupling reaction. This technology adapted Fmoc/tBu chemistry to solution-phase in a much more economically feasible manner, in that it allows for facile purification through precipitation instead of column chromatography or recrystallization. However, an inherent issue with GAP peptide synthesis lies in the method of manufacture of the C-terminal GAP protecting group. While the starting materials required from the synthesis are the cheap, the processes disclosed can be very time consuming, often taking days, and certain steps are difficult to replicate on a large scale. Certain reagents used in the syntheses either require extreme conditions or produce problematic byproducts. Specifically, oxidation with potassium permanganate generates manganese dioxide, a very fine powder which requires either a centrifuge or celite filtration, or both, to remove. Some of the methods disclosed in the '809A1 application also require the use of butyllithium (nBuLi), a pyrophoric reagent; the use of this reagent poses obvious safety risks and also often requires the reaction to be cooled down to −80° C. to avoid undesired side reactions.

There are many other potential uses for GAP protecting groups outside of imine protection and peptide chemistry, but no matter the desired use, the creation of cheap and easy methods of manufacturing GAP groups is of the utmost importance. It is therefore a need in the art to develop methods of GAP group manufacture that are as scalable as possible, avoiding extreme temperature control, problematic byproducts, and dangerous reagents as much as possible.

SUMMARY OF THE INVENTION

The present disclosure addressed failings in the art by providing methods of synthesizing GAP protecting groups that circumvent the need for extreme temperature control, centrifuge and/or extremely fine filtration steps, and/or dangerous reagents. By utilizing unique protecting group strategies and safer organometallic chemistry, synthesis strategies are presented that are economically feasible, scalable, and useful for the commercial production of GAP protecting groups for a myriad of uses.

It is therefore an object of the present disclosure to provide a novel synthesis method to form GAP groups such as HOBnDpp, a C-terminal GAP protecting group used in GAP peptides synthesis. Currently, the most commonly used methods of synthesis require oxidation with potassium permanganate, lithium-halogen exchange with nBuLi, reduction with sodium borohydride, reflux with an alcohol solvent, or all of these reactions, which is problematic from both a scalability perspective and a safety perspective.

In one aspect, a synthesis method that avoids oxidation, esterification, and reduction is presented. In a non-limiting example, the present invention utilizes 4-bromobenzylalcohol as a starting material, wherein the benzyl alcohol is selectively and orthogonally protected to insulate it from lithium-halogen exchange and substitution reactions that replace the bromine with a phosphine oxide moiety. Because the benzyl alcohol is already formed, no oxidation of the benzyl carbon with subsequent esterification and reduction is needed. This circumvents the formation of manganese dioxide, a very fine and difficult to remove byproduct formed by potassium permanganate oxidation, and it also significantly reduces the time and hardship of the synthesis; esterification often takes upwards of 12 hours at reflux temperatures, and reduction with a reagent such as sodium borohydride can be just as time-consuming as well as dangerous because of the evolution of hydrogen gas. The disclosed invention avoids all three of these reactions, greatly improving the ease and scalability of HOBnDpp synthesis.

In another aspect, a synthesis method that avoids the use of butyllithium reagents, oxidation, esterification, and reduction is presented. In a non-limiting example, the method again utilizes protected 4-bromobenzylalcohol as a starting material, reaping all of the benefits of a pre-formed alcohol discussed above. However, instead of performing a lithium-halogen exchange, a Grignard reagent is used followed by substitution with a phosphine moiety, greatly increasing the safety and scalability of the synthesis. The lithium-halogen exchange not only uses pyrophoric nBuLi, requiring inert atmosphere and posing a huge safety risk, but it also is recommended that the reaction mixture be cooled down to −80° C. to prevent unwanted side reactions. Conversely, creating a Grignard reagent to facilitate attachment of the phosphine oxide moiety is much easier and safer, requiring reflux temperatures for a short time to form the reagent and only 0° C. during the reaction with the phosphine.

It is another object of the present invention to provide a novel synthesis strategy for other useful derivatives of the traditional HOBnDpp, such as aniline diphenylphosphine oxide, or $NH_2PhDpp$, a GAP group used in forming GAP-linker complexes that facilitate other types of GAP peptide synthesis. In a non-limiting example, 4-nitrobromobenzene is utilized as a starting material without the use of any protecting groups. Either a lithium-halogen exchange or Grignard reagent followed by substitution yields the appropriate phosphine, and subsequent phosphine oxidation and nitro group reduction will then form the desired GAP group.

In another aspect, the present invention provides a set of new protecting groups. In these new groups, the phosphine oxide moieties are in the ortho or meta positions, as opposed to only the para position, relative to the benzyl carbon on traditional GAP protecting groups. Through these new protecting groups, GAP peptide synthesis is also possible, but the steric environment changes the chemistry of C-terminus protection, potentially allowing for acid cleavage of the GAP group at the end of the synthesis and other significant advantages.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure. The figures are used as non-limiting examples, only intended to portray preferred embodiments without limiting the scope of this disclosure.

DETAILED DESCRIPTION OF THE DISCLOSURE

Figure 1:
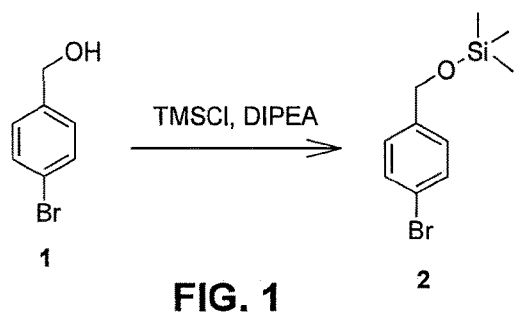
FIG. 1 depicts a step in a non-limiting embodiment of the present invention, in which 4-bromobenzylalcohol is exemplarily protected with a TMS group.

In the Summary of the Invention above and in the Detailed Description of the Invention, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference if made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

The term "first" is used to distinguish one element from another element and is not meant denote that an element is the primary or initial element in any given sequence of elements. For example, "a first amino acid" does not signify that the amino acid is the first in a sequence of amino acids or the first amino acid to be reacted. Instead, "a first amino acid" only indicates that the amino acid is separate and distinguishable from another amino acid, such as "a second amino acid."

The term "coupling reaction" is used to refer generally to the formation of a bond between two constituent molecules facilitated by a "coupling reagent." In peptide chemistry, these coupling reactions can occur via many different mechanisms under many different reaction conditions that can completely depend on the coupling reagent used. For example, a coupling reagent can "activate" the carboxylic acid of a constituent molecule such that the carbonyl carbon can be more prone to nucleophilic attack. Coupling reactions can result in the loss of a water molecule during the formation of the bond between the two constituent molecules (see Chandrudu 2013, Mollica 2013, Shelton 2013, Amblard 2006, Bachem 2016).

In many types of protecting schemes for peptide synthesis, a repetition of similar reactions occurs to grow the peptide chain. Generally, either the N- or C-terminus of each amino acid added to the chain is initially protected, and the other terminus of the amino acid is free to participate in a coupling reaction. After addition to the chain via the initially-free terminus, a deprotection reaction is run, freeing up the protected N- or C-terminus to participate in a subsequent coupling reaction to create a peptide bond with the next amino acid. For example, in Fmoc/tBu-based peptide synthesis, the Fmoc group protects the N-terminus of amino acids, and side chains of amino acids are protected with tBu-based protecting groups, including but not limited to butyl, trityl (triphenylmethyl), Boc (butyloxycarbonyl), Pbf (2,2,4,6,7-pentamethyl-2,3-dihydrobenzofuran-S-sulfonyl), Pmc (2,2,5,7,8-pentamethylchromane-6-sulfonyl), and Acm (acetamidomethyl) (some amino acids do not require sidechain protection because the side-chains are naturally inert to coupling and deprotection conditions). The C-terminus of the primary amino acid in the peptide sequence is connected to and protected by a resin or polymer in SPPS, and a protecting group in SolPPS. The Fmoc/tBu peptide synthesis scheme is designed such that the Fmoc group on the N-termini of amino acids is base-labile, and treatment with the proper deprotection base removes the Fmoc group from the N-termini without interfering with any C-terminus connections or side-chain protections. Once the deprotection reaction is performed, the N-terminus of the primary amino acid is free, while the C-terminus and side chain are protected or otherwise inert. Then, the next amino acid, with the N-terminus Fmoc-protected and the side chain protected or naturally inert, is activated at the free C-terminus with a coupling reagent, and such activation facilitates nucleophilic attack by the free N-terminus of the primary amino acid on the activated carbonyl to form a peptide bond between the primary and next amino acid. This process is repeated until the proper peptide sequence is achieved. After Fmoc deprotection of the final amino acid, the peptide is still protected at the C-terminus and at the side chains. A global deprotection with a strong acid cocktail such as a TFA-based cocktail is then performed to remove all of the side-chain protecting groups; in some cases, the C-terminal resin or protecting group can also be cleaved.

Commonly used abbreviations for different chemical entities and functional groups may be used throughout. "PG" may be used to stand for "protecting group;" "TMS" for "trimethylsilyl;" "MOM" for "methoxymethyl;" "BOM" for "benzyloxymethyl;" "TBS" for "tert-butyldimethylsilyl;" "TIPS" for "triisopropylsilyl;" "TBDPS" for "tert-butyldiphenylsilyl;" "Me" for "methyl;" "tBu" for "tert-butyl;" "alkyl" for "—(CH$_2$)$_n$—CH$_3$ where n=any integer >0 or <20;" "OMe" for "methoxy;" "Ph" for "phenyl;" "2-ClPh" for "2-chlorophenyl;" "4-ClPh" for "4-chlorophenyl;" "3-ClPh" for "3-chlorophenyl;" "3,5-Cl$_2$Ph" for "3,5-dichlorophenyl;" "OTs" for "4-methylbenzenesulfonate;" "OMs" for "methansulfonate;" "OTf" for "trifluoromethanesulfonate."

It is therefore an embodiment of the present disclosure to provide an improved synthesis strategy for the creation of GAP protecting groups used in multiple iterations of GAP peptide synthesis. In designing this method, it was apparent that the method should seek to be as economical, safe, and scalable as possible while maintaining benefits of known synthesis strategies, namely facile purification and isolation through precipitation as opposed to column chromatography or recrystallization. The method would need to be designed to address some specific issues, including shortening the time of synthesis, avoiding undesirable byproducts, replacing undesirable reagents, and adapting the reaction conditions to be more amenable to a large-scale synthesis.

In one embodiment, the present invention provides a method of synthesizing a protecting group, wherein the protecting group is selected from a group consisting of:

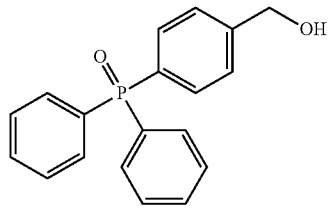

(1A)

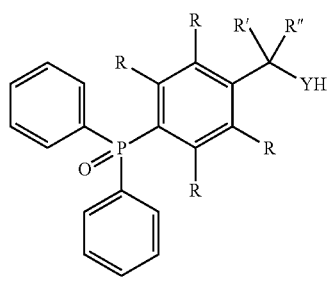

(1B)

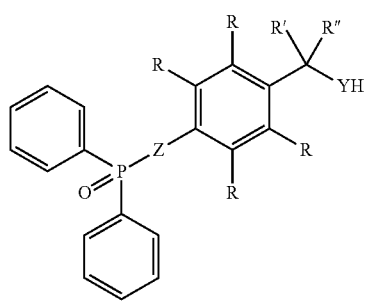

(1C)

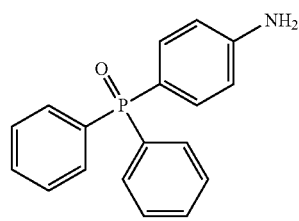

(1D)

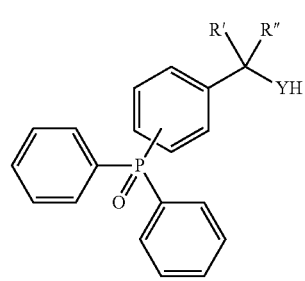

(1E)

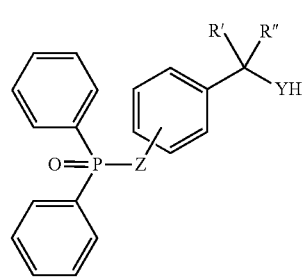

(1F)

wherein:
R is selected from the group consisting of: H, Me, and OMe;
Y is selected from the group consisting of: O, S, and NH;
Z is selected from the group consisting of: O, S, NMe, and NH;
R' is selected from the group consisting of: H, Me, iPr, tBu, Ph, 2-ClPh, 4-ClPh, 3-ClPh, 3,5-Cl2Ph, —(CH2)n-CH3 where n=any integer >0 or <20; and
R" is selected from the group consisting of: H, Me, iPr, tBu, Ph, 2-ClPh, 4-ClPh, 3-ClPh, 3,5-Cl2Ph, —(CH2)n-CH3 where n=any integer >0 or <20.

In another embodiment, the present invention provides a method of forming a protecting group:

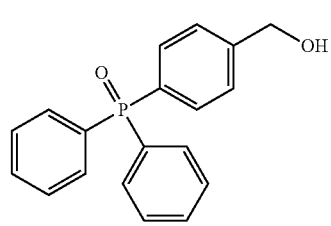

(1A)

which is produced by the following:

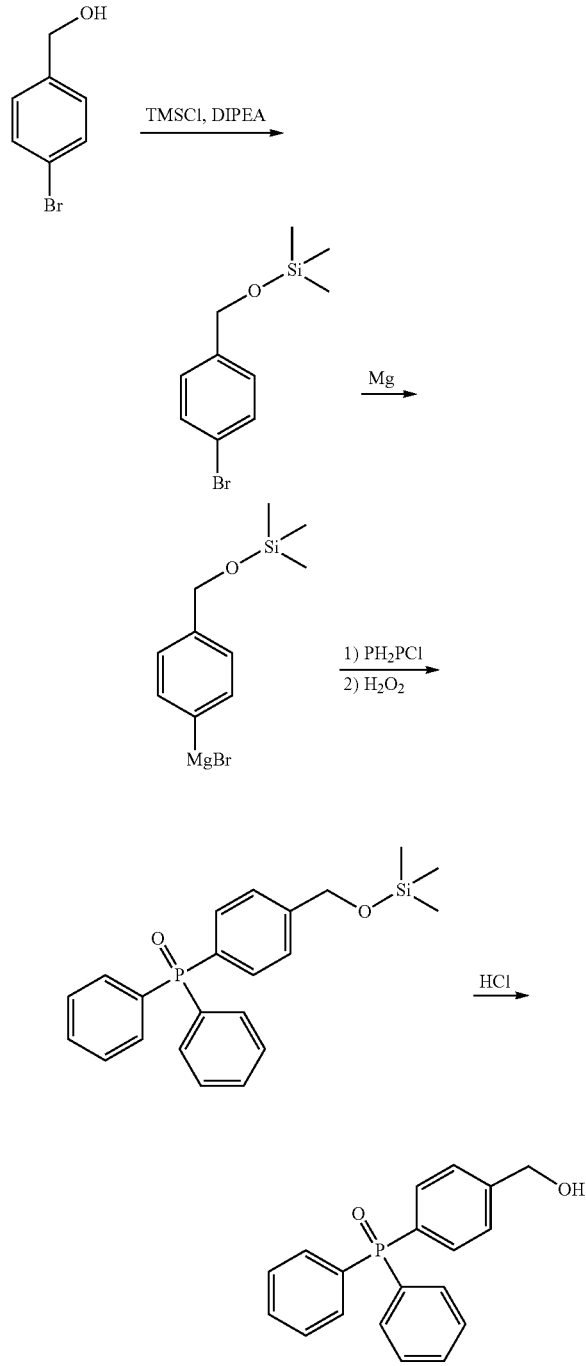

wherein, said protecting group is formed by stirring trimethylsilyl chloride (TMSCl) and DIPEA with 4-bromobenzylalcohol at 0° C.; isolating the TMS-protected bromobenzylalcohol; refluxing the TMS-protected product with magnesium in tetrahydrofuran; slowly adding diphenylchlorophosphine to the reaction at 0° C.; stirring the resulting phosphine moiety with hydrogen peroxide; and removing the TMS group with 2M HCl (aq).

In another embodiment, the present invention discloses a method of synthesizing a protecting group:

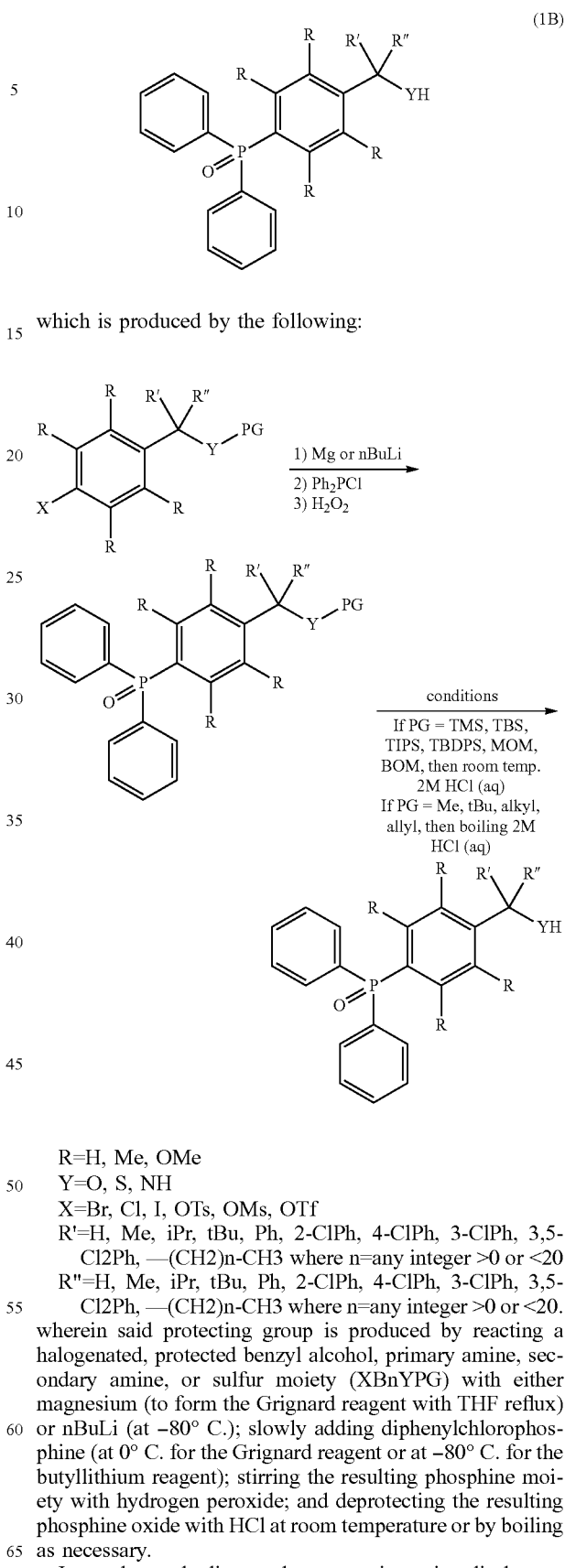

which is produced by the following:

R=H, Me, OMe
Y=O, S, NH
X=Br, Cl, I, OTs, OMs, OTf
R'=H, Me, iPr, tBu, Ph, 2-ClPh, 4-ClPh, 3-ClPh, 3,5-Cl2Ph, —(CH2)n-CH3 where n=any integer >0 or <20
R"=H, Me, iPr, tBu, Ph, 2-ClPh, 4-ClPh, 3-ClPh, 3,5-Cl2Ph, —(CH2)n-CH3 where n=any integer >0 or <20.

wherein said protecting group is produced by reacting a halogenated, protected benzyl alcohol, primary amine, secondary amine, or sulfur moiety (XBnYPG) with either magnesium (to form the Grignard reagent with THF reflux) or nBuLi (at −80° C.); slowly adding diphenylchlorophosphine (at 0° C. for the Grignard reagent or at −80° C. for the butyllithium reagent); stirring the resulting phosphine moiety with hydrogen peroxide; and deprotecting the resulting phosphine oxide with HCl at room temperature or by boiling as necessary.

In another embodiment, the present invention discloses a method of forming protecting group:

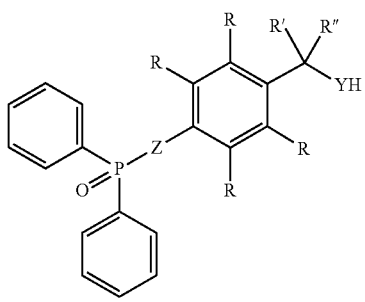

which is produced by the following:

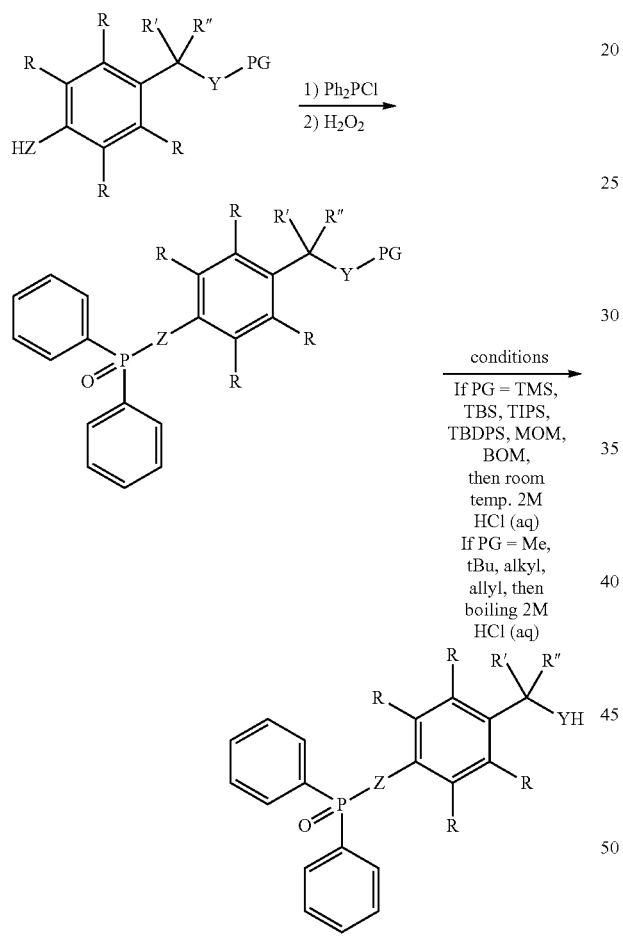

R=H, Me, OMe
Y=O, S, NH
Z=O, S, NMe, NH
R'=H, Me, iPr, tBu, Ph, 2-ClPh, 4-ClPh, 3-ClPh, 3,5-Cl2Ph, —(CH2)n-CH3 where n=any integer >0 or <20
R"=H, Me, iPr, tBu, Ph, 2-ClPh, 4-ClPh, 3-ClPh, 3,5-Cl2Ph, —(CH2)n-CH3 where n=any integer >0 or <20.

wherein a phenyl ring with a protected alcohol, sulfur, or amine moiety, and a free alcohol, sulfur, or amine moiety (HZBnYPG), is reacted with diphenylchlorophosphine; the resulting phosphine is oxidized with hydrogen peroxide; and the protecting group is removed with 2M HCl (room temperature or boiling as necessary).

In another embodiment, the present invention discloses a method of forming protecting group:

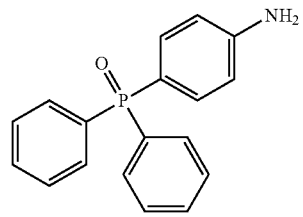

which is produced by the following:

R=H, Me, OMe
X=Br, Cl, I, OTs, OMs, OTf wherein halogenated nitrobenzene is reacted with magnesium (at reflux to yield Grignard reagent) or nBuLi at −80° C.; diphenylchlorophosphine is slowly added (at 0° C. for Grignard reagent or −80° C. for butyllithium reagent); the resulting phosphine product is oxidized with hydrogen peroxide; and the nitro group is subsequently reduced to a primary amine with a reducing agent such as sodium borohydride or hydrogen gas with transition metal catalysts.

In another embodiment, the present invention discloses a method of forming protecting group:

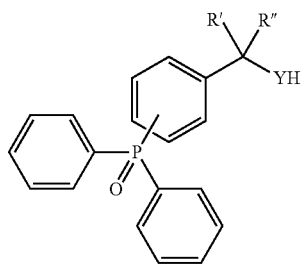 (1E)

which is produced by the following:

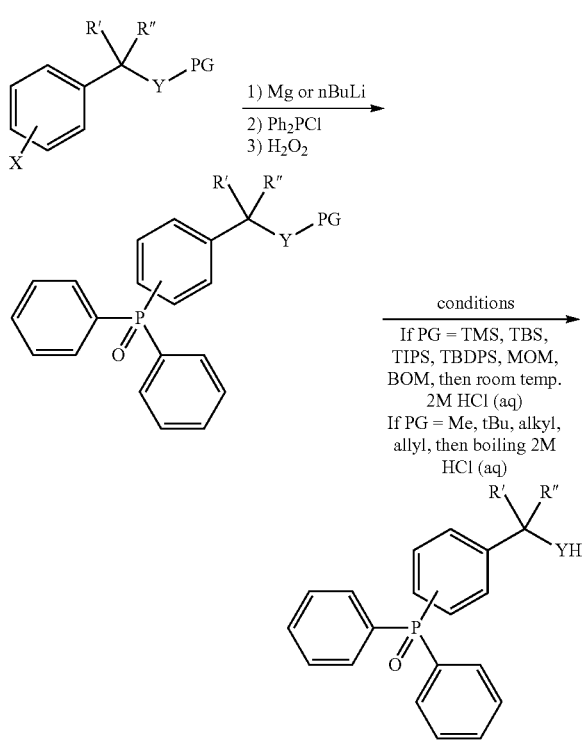

Y=O, S, NH
X=Br, Cl, I, OTs, OMs, OTf
R'=H, Me, iPr, tBu, Ph, 2-ClPh, 4-ClPh, 3-ClPh, 3,5-Cl2Ph, —(CH2)n-CH3
where n=any integer >0 or <20
R''=H, Me, iPr, tBu, Ph, 2-ClPh, 4-ClPh, 3-ClPh, 3,5-Cl2Ph, —(CH2)n-CH3
where n=any integer >0 or <20 wherein said protecting group is produced by reacting a protected benzyl alcohol, primary amine, secondary amine, or sulfur moiety (XBnYPG) that is halogenated at any available para, ortho, or meta position with either magnesium (to form the Grignard reagent with THF reflux) or nBuLi (at −80° C.); slowly adding diphenylchlorophosphine (at 0° C. for the Grignard reagent or at −80° C. for the butyllithium reagent); stirring the resulting phosphine moiety with hydrogen peroxide; and deprotecting the resulting phosphine oxide with HCl at room temperature or by boiling as necessary. In this particular embodiment, the resulting diphenylphosphine oxide can be attached in any of the available para, ortho, or meta positions on the benzene ring.

In another embodiment, the present invention discloses a method of forming protecting group:

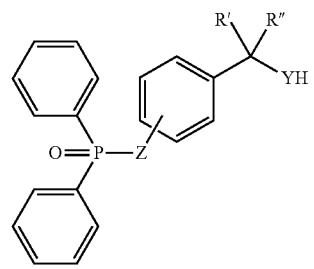 (1F)

which is produced by the following:

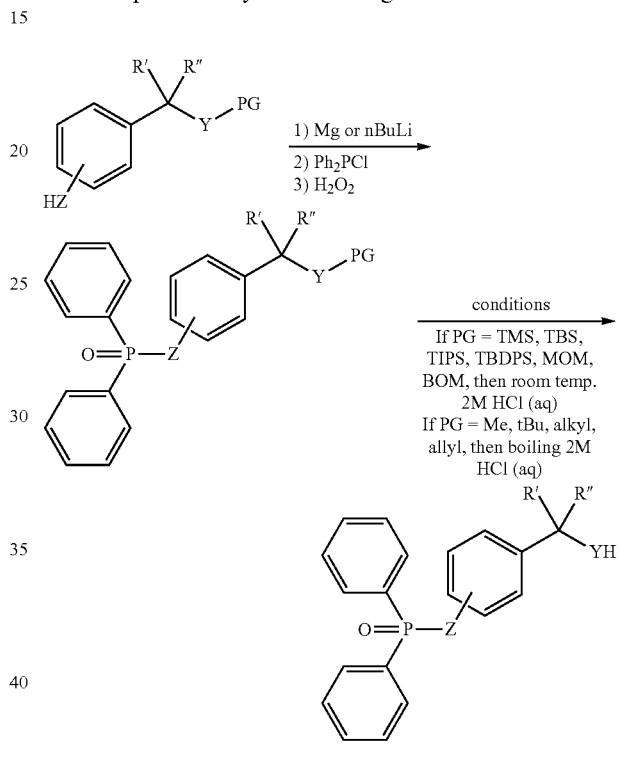

R=H, Me, and OMe;
Y=O, S, and NH; and
Z=O, S, NMe, and NH.
R'=H, Me, iPr, tBu, Ph, 2-ClPh, 4-ClPh, 3-ClPh, 3,5-Cl2Ph, —(CH2)n-CH3
where n=any integer >0 or <20
R''=H, Me, iPr, tBu, Ph, 2-ClPh, 4-ClPh, 3-ClPh, 3,5-Cl2Ph, —(CH2)n-CH3
where n=any integer >0 or <20.

wherein a phenyl ring with a protected alcohol, sulfur, or amine moiety, and a free alcohol, sulfur, or amine moiety (HZBnYPG), is reacted with diphenylchlorophosphine; the resulting phosphine is oxidized with hydrogen peroxide; and the protecting group is removed with 2M HCl (room temperature or boiling as necessary). In this non-limiting embodiment, the diphenylphosphine oxide can be attached to the phenyl ring via the previously free alcohol, sulfur, or amine moiety in any of the available para, ortho, or meta positions.

In another embodiment, the present invention discloses a method of performing Group Assisted Purification (GAP) peptide synthesis, wherein the method comprises the steps of attaching protecting group 1E or 1F to an amino acid via the nucleophilic moiety followed by Fmoc-tBu-based solution phase peptide synthesis (SolPPS) coupling reactions on the resulting amino acid having the attached protecting group. Such method of GAP-PS may further include the reaction occurring in ethyl acetate, dichloromethane, or dimethylformamide.

The principles discussed herein may be embodied in many different forms. The preferred embodiments of the present disclosure will now be described where for completeness, reference should be made at least to the Figures.

Figure 5:
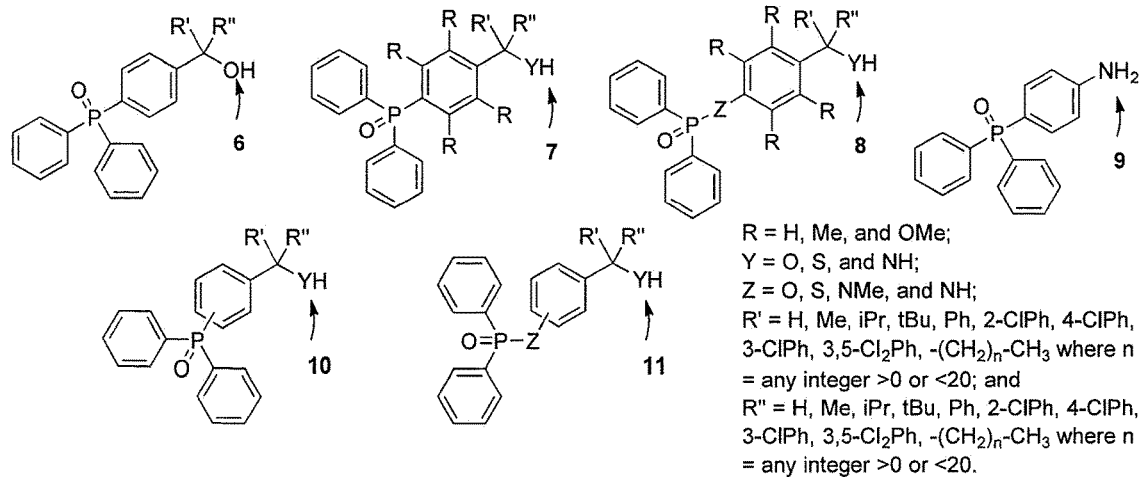
FIG. 5 depicts non-limiting, representative protecting groups that can be synthesized using the present invention. The nucleophilic moiety of each depicted protecting group is labelled.
Figure 11:
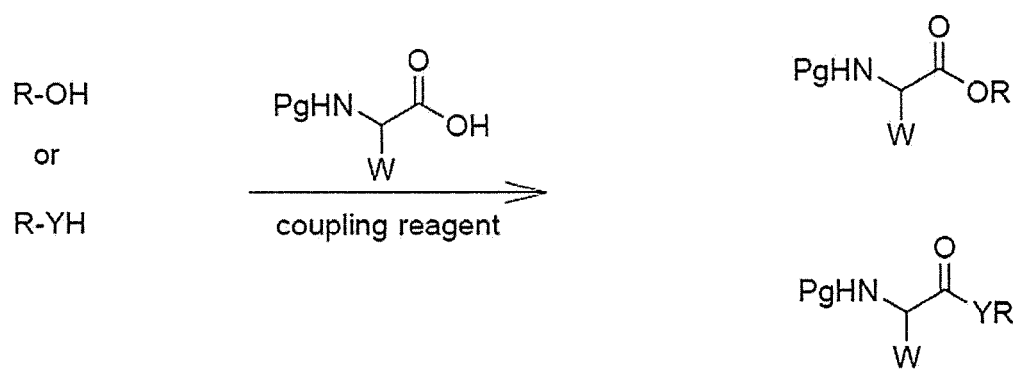
FIG. 11 depicts, as a non-limiting example, the attachment of a protecting group from FIG. 5 to a general amino acid to protect the C-terminus of the amino acid.

FIG. 5 depicts representative protecting groups that can be synthesized using the present invention. In all of the above embodiments, and as a non-limiting example, the final step in the synthesis yields a nucleophilic alcohol, sulfur, or amine moiety 6, 7, 8, 9, 10, 11 (FIG. 5) on the protecting group that can be reacted with a constituent of a molecule of interest to effectuate "protection" of that particular constituent. In a non-limiting example, the nucleophilic moiety from a protecting group shown in FIG. 5 can be reacted with an activated C-terminus of an amino acid to yield a C-terminus protected amino acid (FIG. 11). GAP peptides synthesis can then proceed in the C to N direction.

Figure 6:
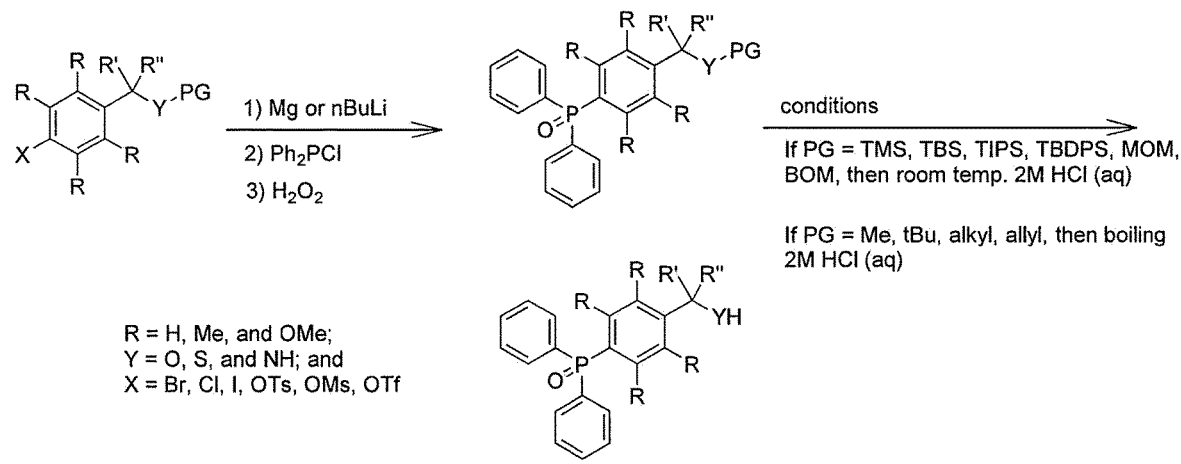
FIG. 6 depicts a schematic by which multiple protecting groups, including some of those of FIG. 5, can be synthesized.
Figure 7:
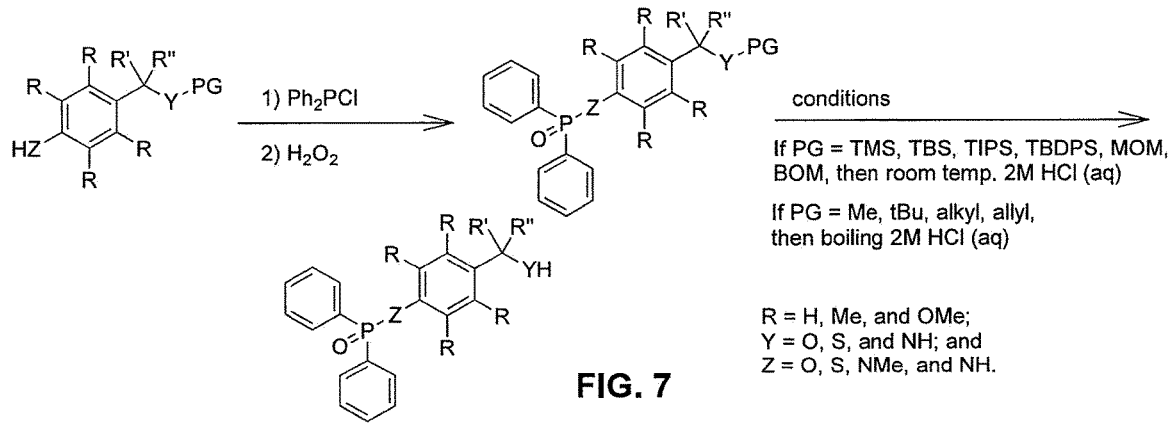
FIG. 7 depicts a schematic by which multiple protecting groups, including some of those of FIG. 5, can be synthesized.

FIGS. 6-7 depict other non-limiting embodiments of the present invention to yield protecting groups of different makeup and uses.

Figure 8:
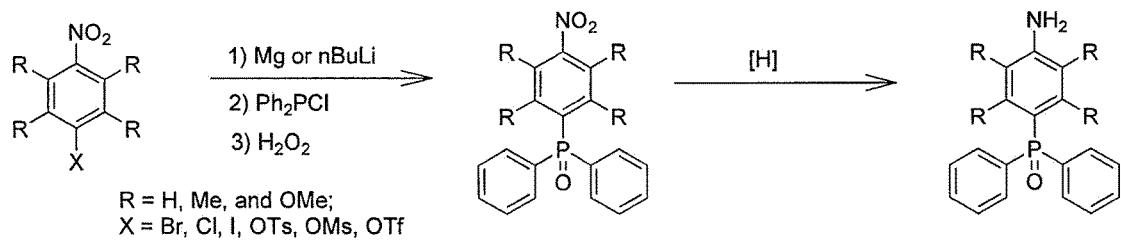
FIG. 8 depicts, as a non-limiting example, a schematic for synthesizing aniline diphenylphosphine oxide from halogenated nitrobenzene.

FIG. 8 depicts a schematic for synthesizing the protecting group aniline diphenylphosphine oxide, or $NH_2PhDpp$.

Figure 9:
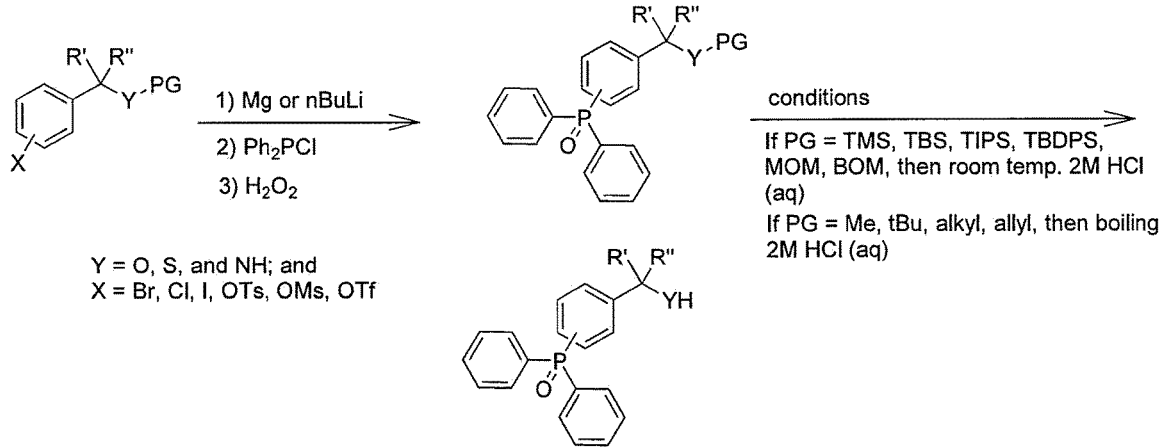
FIG. 9 depicts a schematic by which multiple protecting groups, including some of those of FIG. 5, can be synthesized.

FIG. 9 depicts a non-limiting example of the synthesis of a protecting group, wherein the diphenylphosphine oxide moiety is optionally in the para, ortho, or meta position relative to the nucleophilic moiety.

Figure 10:
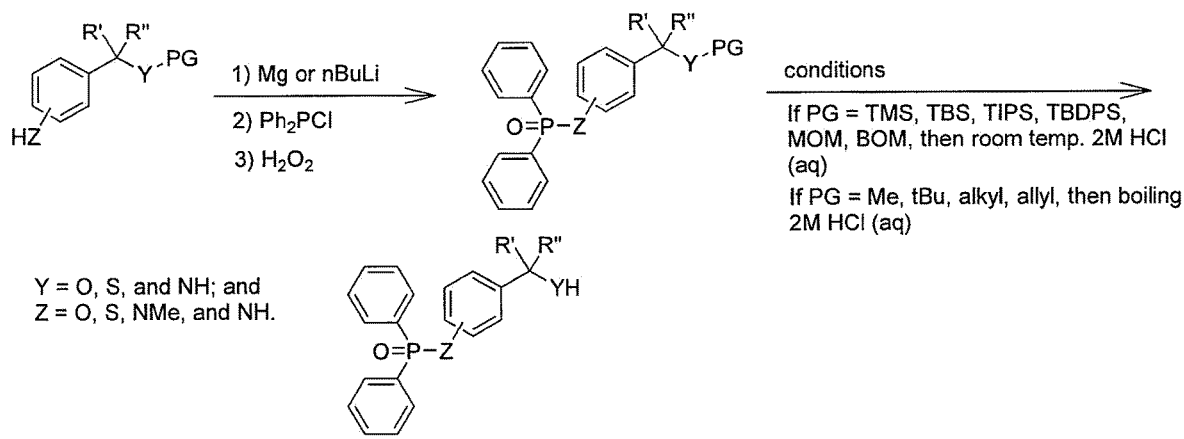
FIG. 10 depicts a schematic by which multiple protecting groups, including some of those of FIG. 5, can be synthesized.

FIG. 10 depicts a non-limiting example of the synthesis of a protecting group, wherein the diphenylphosphine oxide moiety (attached via an alcohol, sulfur, amine, or amino methyl group) is optionally in the para, ortho, or meta position relative to the nucleophilic moiety.

Example 1

For a first application of a new protecting group synthesis method, and as a non-limiting example of the present invention, the GAP protecting group HOBnDpp was formed.

Synthesis of TMS-protected 4-bromobenzylalcohol 1. 39 g of 1 (FIG. 1) was first dissolved in 500 mL diethyl ether in a 1 L round-bottomed flask and cooled down to 0° C. in an ice bath. 36 mL of DIPEA was added to the solution, followed by a dropwise addition of 27 mL TMS chloride, and the reaction was stirred for about thirty minutes. DIPEA hydrochloride precipitated as a white solid and was filtered out, leaving 2 dissolved in diethyl ether. This solution was concentrated down to an oil and subjected directly to the next reaction.

Figure 2:
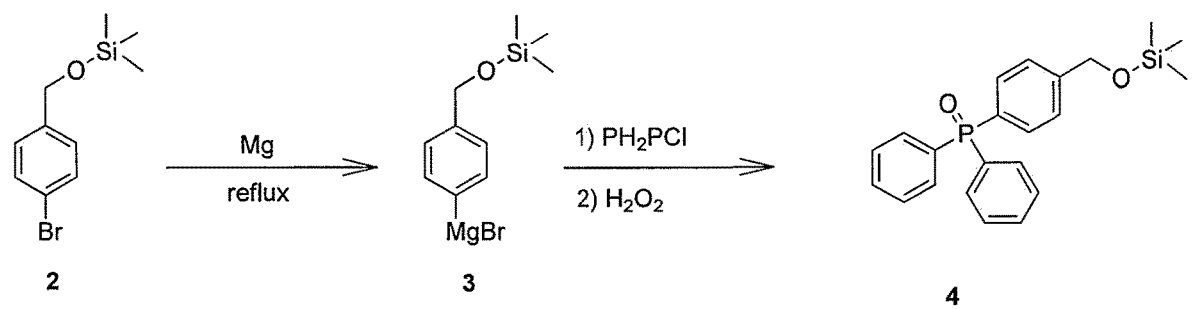
FIG. 2 depicts a step in a non-limiting embodiment of the present invention, in which TMS-protected 4-bromobenzylalcohol is transformed into a Grignard reagent and subsequently converted to TMS-protected HOBnDpp.

Synthesis of Grignard reagent 3.2 from the previous reaction was dissolved in 300 mL of dry, distilled THF. 3.8 g of magnesium shavings were added to the solution and the reaction was stirred at reflux for about three hours, or until all of the magnesium dissolved, to obtain 3 (FIG. 2). This product remained preserved in THF solution under nitrogen atmosphere and was directly subjected to the next reaction.

Synthesis of protected TMSOBnDpp 4.3 from the previous reaction dissolved in THF was cooled down to 0° C., and 15 mL of diphenylchlorophosphine was slowly added and stirred for about thirty minutes. 100 mL of $H_2O$ was added to quench the reaction and subsequently extracted, and 30 mL of 30% hydrogen peroxide was added and stirred with the solution for about fifteen minutes to yield 4 in the THF layer (FIG. 2). The water layer was extracted, and the THF layer with 4 was directly subjected to the next reaction.

Figure 4:
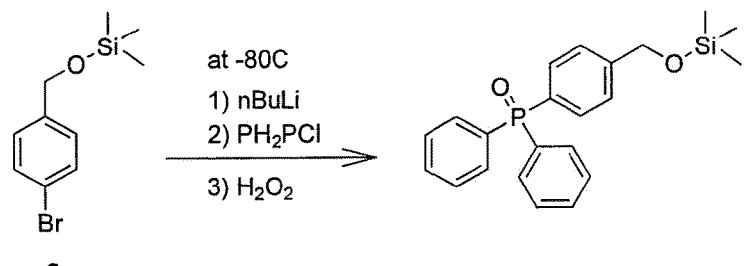
FIG. 4 depicts a step in a non-limiting embodiment of the present invention, in which TMS-protected 4-bromobenzylalcohol is converted to TMS-protected HOBnDpp using a butyllithium reagent.

Lithium-halogen exchange in lieu of Grignard reagent. 2 (FIG. 1) was dissolved in 250 mL of dry, distilled THF, and the solution was cooled down to −80° C. in a dry ice/acetone bath. 100 mL of 1.6M nBuLi solution in hexanes was added dropwise under a nitrogen atmosphere, followed by a dropwise addition of diphenylchlorophosphine. That was allowed to stir for about thirty minutes, and after addition of 100 mL water, 30 mL of 30% hydrogen peroxide was added and stirred with the reaction mixture for about fifteen minutes to yield 4 (FIG. 4).

Figure 3:
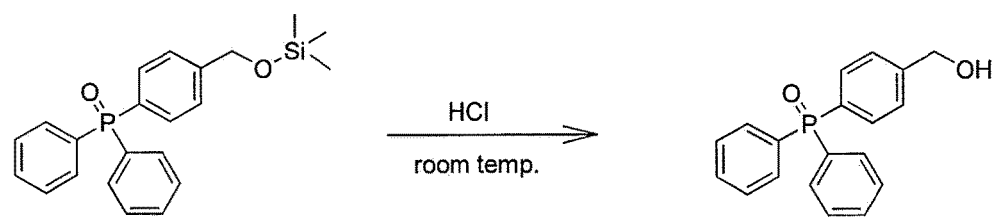
FIG. 3 depicts a step in a non-limiting embodiment of the present invention, in TMS-protected HOBnDpp is TMS-deprotected.

Synthesis of HOBnDpp 5. 300 mL of 2M HCl (aq) was added to 4 dissolved in THF from the previous reaction and stirred overnight. The HCl layer was then extracted, and the THF layer was dried and then concentrated to dryness to yield 5 at about 95% purity (FIG. 3).

General methods: All solvents were ACS grade and used without additional purification. LCMS analysis was conducted using a Thermo TSQ Quantum Access Mass Spectrometer equipped with a PAL autosampler and Agilent solvent pump.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among various software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad combinations are possible in achieving the functions, features, and preferences described herein. Moreover, the scope of the present disclosure covers conventionally known manners for carrying out the described features as well as those variations and modifications that may be made to the processes, composition, or compounds described herein as would be understood by those skilled in the art now and hereafter.

Furthermore, the embodiments of methods presented and described as diagrams, schematics or flowcharts in this disclosure (such as the Figures) are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently. While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

RELATED REFERENCES

The below references are incorporated herein by reference as examples.

An, G.; Seifert, C.; Li, G. N-Phosphonyl/phosphinyl imines and group-assisted purification (GAP) chemistry/technology. Org. Biomol. Chem. 2015, 13, 1600-1617.

Ai, T.; Li, G. Chiral N-phosphonyl imine chemistry: Asymmetric synthesis of αβ-diamino esters by reacting phosphonyl imines with glycine enolates. Bioorg. Med. Chem. Lett. 2009, 19, 3967-3969.

Han, J.; Ai, T.; Nguyen, T.; Li, G. Chiral N-phosphonyl imine chemistry: asymmetric additions of ester enolates for the synthesis of β-amino acids. Chem. Biol. Drug Des. 2008, 72, 120-126.

Kattamuri, P. V.; Ai, T.; Pindi, S.; Sun, Y.; Gu, P.; Shi, M.; Li, G. Asymmetric Synthesis of α-Amino-1,3-dithianes via Chiral N-Phosphonyl Imine-Based Umpolung Reaction Without Using Chromatography and Recrystallization. J. Org. Chem. 2011, 76, 2792-2797.

Kattuboina, A.; Kaur, P.; Nguyen, T.; Li, G. Chiral N-phosphonyl imine chemistry: asymmetric 1,2-additions of allylmagnesium bromides. Tetrahedron Lett. 2008, 49, 3722-3724.

Kattuboina, A.; Li, G. Chiral N-phosphonyl imine chemistry: new reagents and their applications for asymmetric reactions. Tetrahedron Lett. 2008, 49, 1573-1577.

Kaur, P.; Wever, W.; Pindi, S.; Milles, R.; Gu, P.; Shi, M.; Li, G. The GAP chemistry for chiral N-phosphonyl imine-based Strecker reaction. Green Chem. 2011, 13, 1288-1292.

Pindi, S.; Kaur, P.; Shakya, G.; Li, G. N-Phosphinyl Imine Chemistry (I): Design and Synthesis of Novel N-Phosphinyl Imines and their Application to Asymmetric aza-Henry Reaction. Chem. Biol. Drug. Des. 2011, 77, 20-29.

Xie, J.-b.; Luo, J.; Winn, T. R.; Cordes, D. B.; Li, G. Group-assisted purification (GAP) chemistry for the synthesis of Velcade via asymmetric borylation of Nphosphinylimines. Beilstein J. Org. Chem. 2014, 10, 746-751.

Dailler, D.; Danoun, G.; Baudoin, O. A General and Scalable Synthesis of Aeruginosin Marine Natural Products Based on Two Strategic C(sp(3))-H Activation Reactions. Angewandte Chemie-International Edition 2015, 54, 4919-4922.

Kaufmann, E.; Hattori, H.; Miyatake-Ondozabal, H.; Gademann, K. Total Synthesis of the Glycosylated Macrolide Antibiotic Fidaxomicin. Organic Letters 2015, 17, 3514-3517.

Sharma, P. K.; Romanczyk, L. J.; Kondaveti, L.; Reddy, B.; Arumugasamy, J.; Lombardy, R.; Gou, Y.; Schroeter, H. Total Synthesis of Proanthocyanidin A1, A2, and Their Stereoisomers. Organic Letters 2015, 17, 2306-2309.

Wuts, P. G. M. Greene's Protective Groups in Organic Synthesis. 5 ed.; John Wiley & Sons, Inc: New Jersey, 2014.

Isidro-Llobet, A.; Alvarez, M.; Albericio, F. Amino Acid-Protecting Groups. Chem. Rev. 2009, 109, 2455-2504.

Behrendt, R.; Huber, S.; Marti, R.; White, P. New t-butyl based aspartate protecting groups preventing aspartimide formation in Fmoc SPPS. Journal of Peptide Science 2015, 21, 680-687.

Chandrudu, S.; Simerska, P.; Toth, I. Chemical Methods for Peptide and Protein Production. Molecules 2013, 18, 4373.

Mochizuki, M.; Tsuda, S.; Tanimura, K.; Nishiuchi, Y. Regioselective Formation of Multiple Disulfide Bonds with the Aid of Postsynthetic S-Tritylation. Organic Letters 2015, 17, 2202-2205.

Merrifield, R. B. Solid Phase Peptide Synthesis. I. The Synthesis of a Tetrapeptide. J. Am. Chem. Soc. 1963, 85, 2149.

Mollica, A.; Pinnen, F.; Azzurra, S.; Costante, R. The Evolution of Peptide Synthesis: From Early Days to Small Molecular Machines. Curr. Bioact. Compd. 2013, 9, 184-202.

Shelton, P. T.; Jensen, K. J. Linkers, Resins, and General Procedures for Solid-Phase Peptide Synthesis. In Peptide Synthesis and Applications, 2nd Edition, Jensen, K. J.; Shelton, P. T.; Pedersen, S. L., Eds. Humana Press Inc: Totowa, 2013; Vol. 1047, pp 23-41.

An, G.; Seifert, C.; Sun, H.; Pan, Y.; Li, G. Group-Assisted Purification (GAP) for Protection of Amino Acids Using N-Phosphonyl Functional Groups. Heterocycles 2015, 90, 344-356.

An, G.; Zhou, W.; Xu, X.; Pan, Y.; Li, G. Solution-Phase-Peptide Synthesis Without Purification of Column Chromatography and Recrystallization by Protecting Amino Acid Esters with Phosphinyl Chloride. Heterocycles 2015, 90, 1405-1418.

Wu, J.; An, G.; Lin, S.; Xie, J.; Zhou, W.; Sun, H.; Pan, Y.; Li, G. Solution phase peptide synthesis via the group-assisted purification (GAP) chemistry without using chromatography and recrystallization. Chem. Commun. 2014, 50, 1259-1261.

Brieke, C.; Cryle, M. J. A Facile Fmoc Solid Phase Synthesis Strategy To Access Epimerization-Prone Biosynthetic Intermediates of Glycopeptide Antibiotics. Organic Letters 2014, 16, 2454-2457.

Chen, C.-C.; Rajagopal, B.; Liu, X. Y.; Chen, K. L.; Tyan, Y.-C.; Lin, F.; Lin, P.-C. A mild removal of Fmoc group using sodium azide. Amino Acids 2014, 46, 367-374.

Spinella, M.; De Marco, R.; Belsito, E. L.; Leggio, A.; Liguori, A. The dimethylsulfoxonium methylide as unique reagent for the simultaneous deprotection of amino and carboxyl function of N-Fmoc-α-amino acid and N-Fmoc-peptide esters. Tetrahedron 2013, 69, 2010-2016.

Amblard, M.; Enomoto, H.; Subra, G.; Fehrentz, J.-A.; Martinez, J. The Fundamentals of Fmoc Solid-Phase Peptide Synthesis. Idenshi Igaku Mook 2012, 21, 36-42.

Shi, M.; Yang, Y.; Zhou, X.; Cai, L.; Fang, C.; Wang, C.; Sun, H.; Sun, Y.; Gao, Y.; Gu, J.; Fawcett, J. P. Determination of thymopentin in beagle dog blood by liquid chromatography with tandem mass spectrometry and its application to a preclinical pharmacokinetic study. Journal of Separation Science 2015, 38, 1351-1357.

Zhu, M.-X.; Wan, W.-L.; Li, H.-S.; Wang, J.; Chen, G.-A.; Ke, X.-Y. Thymopentin enhances the generation of T-cell lineage derived from human embryonic stem cells in vitro. Experimental Cell Research 2015, 331, 387-398.

Fu, T. T.; Qiao, H. W.; Peng, Z. M.; Hu, G. B.; Wu, X. J.; Gao, Y. X.; Zhao, Y. F. Palladium-catalyzed air-based oxidative coupling of arylboronic acids with H-phosphine oxides leading to aryl phosphine oxides. Organic & Biomolecular Chemistry 2014, 12, 2895-2902.

Lawrenson, S. B.; Arav, R.; North, M. The greening of peptide synthesis. Green Chemistry 2017, 19, 1685.

Isidro-Llobet, A.; Alvarez, M.; Albericio, F. Amino Acid-Protecting Groups. Chemical Reviews 2009, 109, 2455-2504.

Jensen, Knud J. Chapter 1: Peptide Synthesis. Pharmaceutical Formulation Development of Peptides and Proteins 2013, pages 1-16.

Amblard, M.; Fehrentz, J. A.; Martinez, J.; Subra, G. Methods and Protocols of Modern Solid Phase Peptide Synthesis. Molecular Biotechnology 2006, 33, 239-254.

Bachem. Tips and Trick for Solid Phase Peptide Synthesis from the Experts at Bachem. Solid Phase Peptide Synthesis 2016, pages 1-55.

P. Wuts and T. Greene, Greene's Protective Groups in Organic Synthesis 4th ed. John Wiley & Sons, 2006.

What is claimed is:

1. A protecting group for chemical synthesis, selected from the group consisting of:

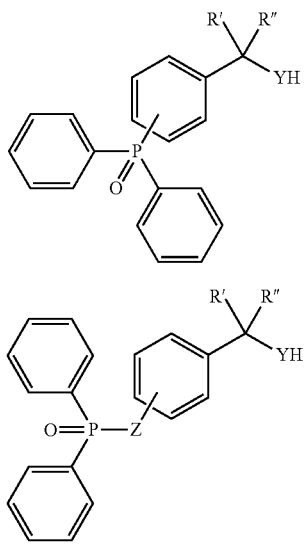

wherein:
in (1E):
  Y is selected from the group consisting of: —S— and —NH—;
  R' is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and
  R" is selected from the group consisting of: Me, iPr, tBu, Ph, 2-ClPh, 4-ClPh, 3- ClPh, 3,5-Cl2Ph, and —(CH2)n-CH3 where n=any integer >0 and <20; and
in (1F):
  Y is selected from the group consisting of: —O—, —S—, and —NH—;
  Z is selected from the group consisting of: —O—, —S—, —NMe, and —NH—;
  R' is selected from the group consisting of: -Me, iPr, tBu, Ph, 2-ClPh, 4-ClPh, 3-ClPh, 3,5-Cl2Ph, and —(CH2)n-CH3 where n=any integer >0 and <20; and
  R" is selected from the group consisting of: Me, iPr, tBu, Ph, 2-ClPh, 4-ClPh, 3-ClPh, 3,5-Cl2Ph, and —(CH2)n-CH3 where n=any integer >0 and <20.

2. A method comprising the step of synthesizing a protecting group, wherein the protecting group is selected from a group consisting of:

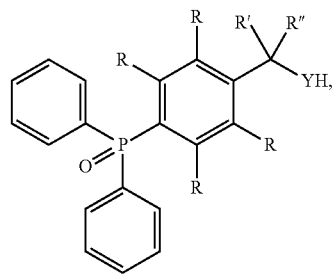

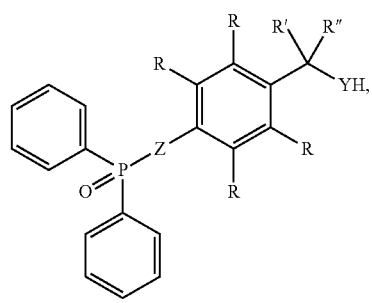

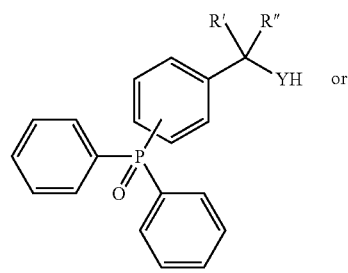

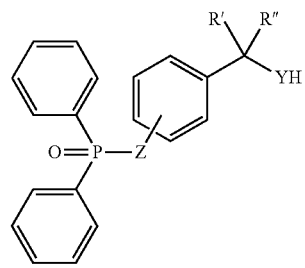

wherein:
in (1B):
  R is selected from the group consisting of: —H, -Me, and —OMe;
  Y is selected from the group consisting of: —S— and —NH—;
  R' is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and
  R" is selected from the group consisting of: Me, iPr, tBu, Ph, 2-ClPh, 4-ClPh, 3-ClPh, 3,5-Cl2Ph, and —(CH2)n-CH3 where n=any integer >0 and <20;
in (1E):
  Y is selected from the group consisting of: —S— and —NH—;
  R' is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and
  R" is selected from the group consisting of: Me, iPr, tBu, Ph, 2-ClPh, 4-ClPh, 3,5-Cl2Ph, and —(CH2)n-CH3 where n=any integer >0 and <20; and in (1C) and (1F):
R is selected from the group consisting of: —H, -Me, and —OMe;
Y is selected from the group consisting of: —O—, —S—, and —NH—;
Z is selected from the group consisting of: —O—, —S—, —NMe, and —NH—;
R' is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and
R" is selected from the group consisting of: Me, iPr, tBu, Ph, 2-ClPh, 4-ClPh, 3-ClPh, 3,5-Cl2Ph, and —(CH2)n-CH3 where n=any integer >0 and <20.

3. The method of claim 2, wherein protecting group:

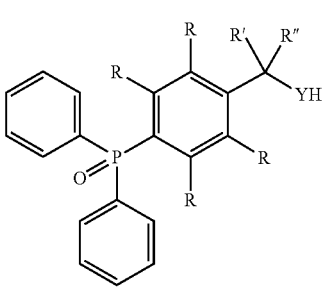

(1B)

is produced by the following:

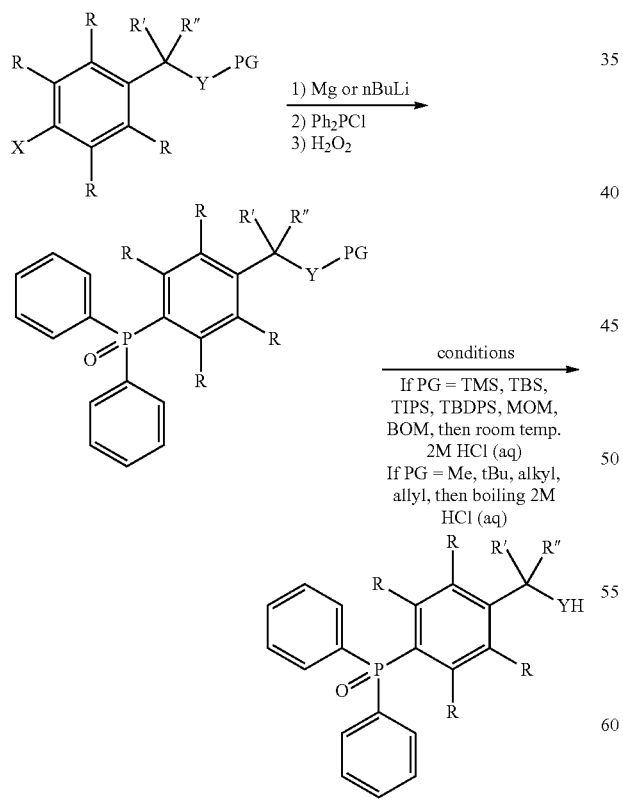

wherein: PG stands for protecting group;
R is selected from the group consisting of: —H, -Me, and —OMe;

Y is selected from the group consisting of: —S— and —NH—;
X is selected from the group consisting of: —Br, —Cl, —I, -OTs, -OMs, and -OTf;
R' is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and
R" is selected from the group consisting of: Me, iPr, tBu, Ph, 2-ClPh, 4-ClPh, 3-ClPh, 3,5-Cl2Ph, and —(CH2)n-CH3 where n=any integer >0 and <20.

4. The method of claim 2, wherein the protecting group (1C) is synthesized by the following reaction:

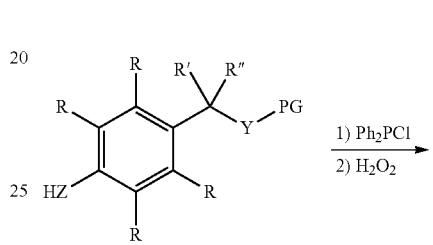

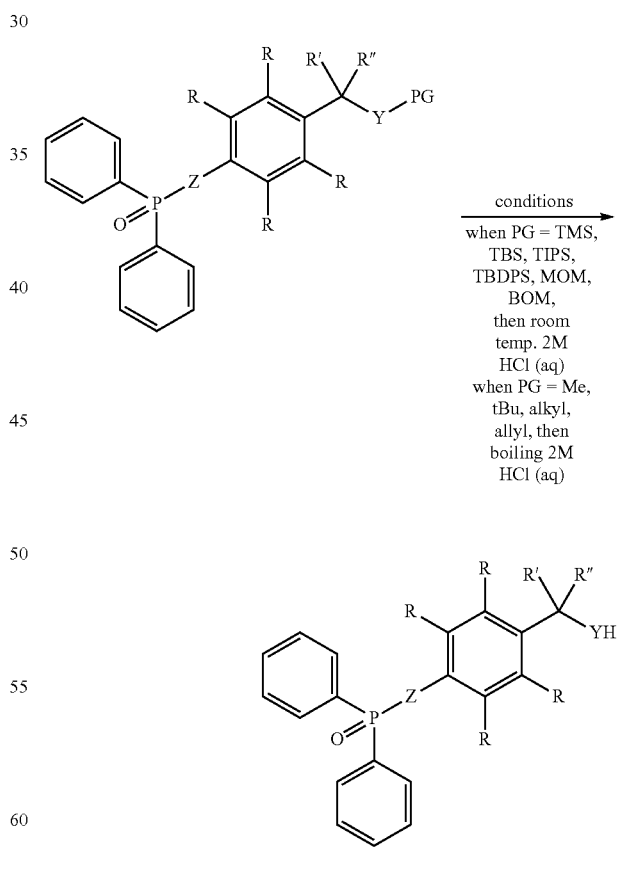

where: PG stands for protecting group; TMS is trimethylsilyl; MOM is methoxymethyl; BOM is benzyloxymethyl; TBS is tert-butyldimethylsilyl; TIPS is triisopropylsilyl; and TBDPS is tert-butyldiphenylsilyl.

5. The method of claim 2, wherein protecting group:

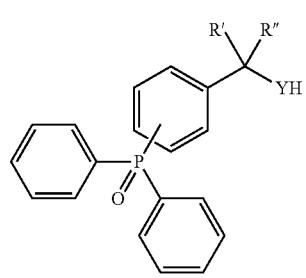

is produced by the following:

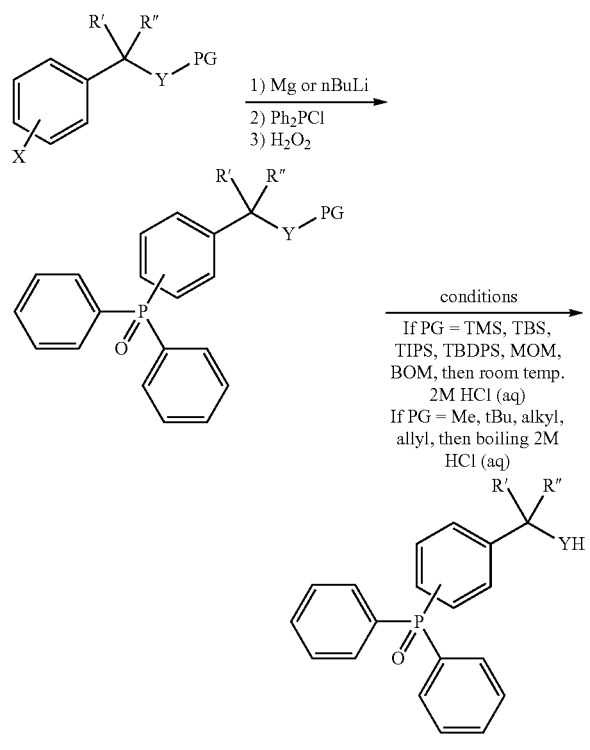

wherein: PG stands for protecting group;
Y is selected from the group consisting of: —S— and —NH—;
X is selected from the group consisting of: —Br, —Cl, —I, -OTs, -OMs, and -OTf;
R' is selected from the group consisting of Me, iPr, tBu, Ph, 2-ClPh, 4-ClPh, 3-ClPh, 3,5-Cl2Ph, and —(CH2)n-CH3 where n=any integer >0 and <20; and
R" is selected from the group consisting of Me, iPr, tBu, Ph, 2-ClPh, 4-ClPh, 3-ClPh, 3,5-Cl2Ph, and —(CH2)n-CH3 where n=any integer >0 and <20.

6. The method of claim 2, wherein the protecting group (1F) is synthesized by the following reaction:

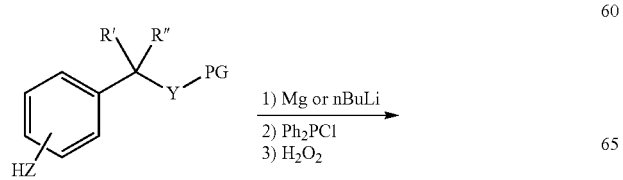

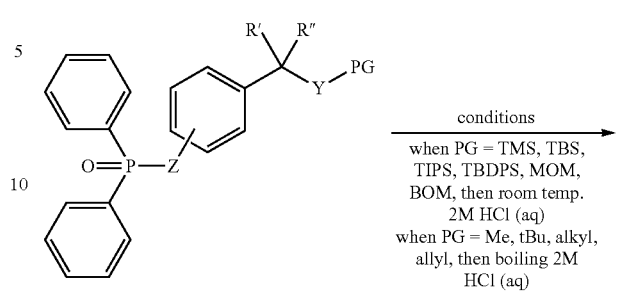

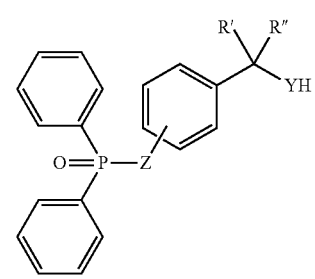

where: P(stands tor protecting group; TMS is trimethylsilyl; MOM is methoxymethyl; BOM is benzyloxymethyl; TBS is tert-butyldimethylsilyl; TIPS is triisopropylsilyl; and TBDPS is tert-butyldiphenylsilyl.

7. A method of performing Group Assisted Purification (GAP) peptide synthesis, wherein the method comprises the steps of attaching a protecting group to an amino acid via a nucleophilic moiety followed by Fmoc-tBu-based solution phase peptide synthesis (SoIPPS) coupling reactions on the resulting amino acid having the attached protecting group; wherein the protecting group comprises at least one of:

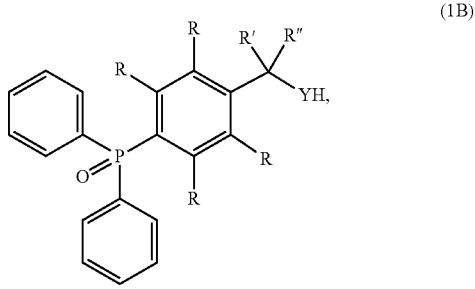

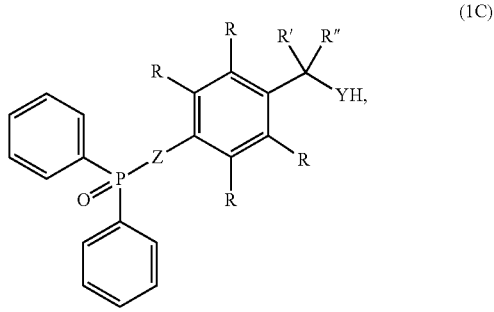

-continued

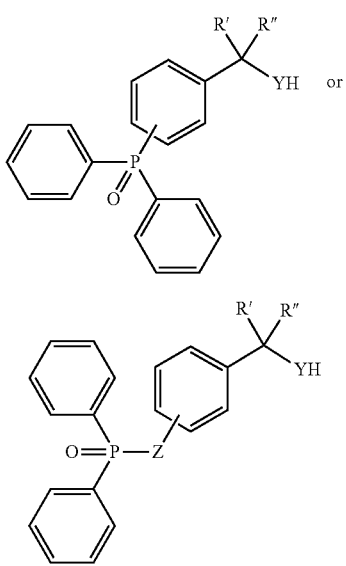

wherein:
in (1B):
R is selected from the group consisting of: —H, -Me, and —OMe;
Y is selected from the group consisting of: —S— and —NH—;
R' is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and
R" is selected from the group consisting of: Me, iPr, tBu, Ph, 2-ClPh, 4-ClPh, 3-ClPh, 3,5-Cl2Ph, and —(CH2)n-CH3 where n=any integer >0 and <20;

in (1E):
Y is selected from the group consisting of: —S—, and —NH—;
R' is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and
R" is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and in (1C) and (1F):
R is selected from the group consisting of: —H, -Me, and —OMe;
Y is selected from the group consisting of: —O—, —S—, and —NH—;
Z is selected from the group consisting of: —O—, —S—, —NMe, and —NH—;
R' is selected from the group consisting of: Me, iPr, tBu, Ph, 2-ClPh, 4-ClPh, 3-ClPh, 3,5-Cl2Ph, and —(CH2)n-CH3 where n=any integer >0 and <20; and
R" is selected from the group consisting of: Me, iPr, tBu, Ph, 2-ClPh, 4-ClPh, 3-ClPh, 3,5-Cl2Ph, and —(CH2)n-CH3 where n=any integer >0 and <20.

8. The method of claim 7, wherein the reactions occur in ethyl acetate.

9. The method of claim 7, wherein the reactions occur in dichloromethane.

10. The method of claim 7, wherein the reactions occur in dimethylformamide.

11. The method of claim 7, wherein the reactions occur in 2-methyltetrahydrofuran.

12. The method of claim 7, wherein the reactions occur in propylene carbonate.

* * * * *